United States Patent [19]

Rosowsky

[11] Patent Number: 4,767,761
[45] Date of Patent: Aug. 30, 1988

[54] ORNITHINE DERIVATIVES AND THEIR USE AS METHOTREXATE-RESISTANT CELL INHIBITORS

[75] Inventor: Andre Rosowsky, Needham, Mass.

[73] Assignee: Dana-Farber Cancer Institute, Inc., Boston, Mass.

[21] Appl. No.: 117,212

[22] Filed: Nov. 4, 1987

[51] Int. Cl.$^4$ .................. A61K 31/495; C07D 475/08
[52] U.S. Cl. ..................................... 514/249; 544/260
[58] Field of Search ......................... 544/260; 514/249

[56] References Cited

U.S. PATENT DOCUMENTS 4,369,319  1/1983  DeGraw, Jr. et al. ............. 544/260

OTHER PUBLICATIONS

Rosowsky et al., J. Med. Chem. vol. 29, pp. 655-660 (1986) and 1703-1709 (1986).

Bodanszky et al., J.A.C.S., vol. 86, pp. 4452-4459 (1964).
Mosmann, J. of Immunol. Methods, vol. 65, pp. 55-63 (1983).

*Primary Examiner*—Mary C. Lee
*Assistant Examiner*—J. Richter

[57] ABSTRACT

Compounds having the structure

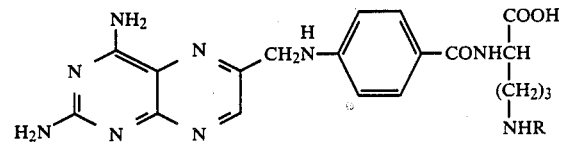

in which R is —CO—Ar—COOR$_1$ where R$_1$ is hydrogen or lower alkyl, and pharmaceutical compositions containing the same exhibiting high growth inhibitory activity against methotrexate resistant cells.

10 Claims, No Drawings

ORNITHINE DERIVATIVES AND THEIR USE AS METHOTREXATE-RESISTANT CELL INHIBITORS

This invention was made with Government support and the U.S. Government has certain rights in the invention.

This invention relates to certain $N^\delta$-acyl derivatives of $N^\alpha$-(4amino-4-deoxypteroyl)-L-ornithine and to pharmaceutical compositions containing the same which exhibit high inhibitory activity against the growth of methotrexate-resistant cells.

$N^\alpha$-(4-Amino- 4-deoxypteroyl)-L-ornithine (hereinafter sometimes called APA—L—Orn) has the structure

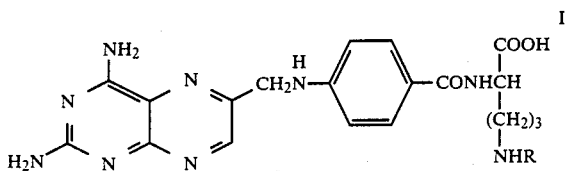

in which R is hydrogen. It has been reported to be a potent inhibitor of dihydrofolate reductase (DHFR) and of folylpolyglutamate synthetase (FPGS), but to be relatively inactive as an inhibitor of cell growth in culture, and it has been suggested that amino-substituted prodrug derivatives of it would be of interest because of possible increased cellular uptake. Rosowsky et al., J. Med. Chem., Vol. 29, pp. 655–660 (1986).

The present invention relates to $N^\delta$-acyl derivatives of APA—L—Orn having the structure I above in which R is —OC—Ar—COOR$_1$ where Ar is an aromatic group and R$_1$ is hydrogen or lower alkyl (1–5 carbon atoms). Such compounds display remarkably high inhibitory activity against the growth of tumor cells resistant to methotrexate, such as the human cell lines SCC 15/R1 and SCC 25/R1, an activity unexpectedly higher than that of other $N^\delta$-acyl derivatives of APA—L—Orn. The compounds of the present invention include those in which Ar is monocyclic or bicyclic aromatic, preferably monocyclic, as well as those in which additional substituent groups are present in the aromatic group such as chlorine, hydroxy or lower alkoxy (1–5 carbon atoms), but the preferred compounds are those in which R is

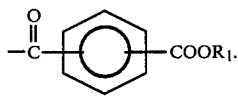

In the preferred compounds the —COOR$_1$ group may be in a position ortho, meta, or para to the

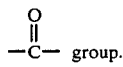

group.

The compounds of the present invention can be made by reacting $N^\alpha$-(4-amino-4-deoxy-$N^{10}$-formylpteroyl)-L-ornithine or its trifluoroacetate salt with the appropriate carboxylic anhydride to form $N^\delta$-acyl-$N^\alpha$-(4-amino-4-deoxy-$N^{10}$-formylpteroyl)-L-ornithine, followed by treating the latter under mild alkaline conditions to cleave the $N^{10}$-formyl group selectively; the cleavage reaction was described by Rosowsky et al., J. Med. Chem., Vol. 29, 1703–1709 (1986). The hemiphthaloyl derivative of APA—L—Orn can also be made by reacting 4-amino-4-deoxy-$N^{10}$-formylpteroic acid sesquihydrate (Rosowsky et al., J. Med. Chem., Vol. 29, pp. 655–660 (1986)) with persilylated $N^\delta$-phthalyl-L-ornithine (Bodanszky et al., J.A.C.S., Vol. 86, 4452–4459 (1964)) to form the $N^{10}$-formyl $N^\delta$-phthalimide derivative followed by simultaneous deformylation and opening of the imide ring under alkaline conditions.

The compounds can be mixed with or dissolved on a conventional pharmaceutically acceptable non-toxic carrier to provide a therapeutic composition. The effective dose of the active agent can readily be determined by simple tests.

EXAMPLE $N^\alpha$-(4-Amino-4-deoxy-$N^{10}$-formylpteroyl)-$N^\delta$-phthalyl-L-ornithine To a suspension of $N^{67}$-phthalyl-L-ornithine hydrochloride (1.19 g, 4 mmol) in CH$_2$Cl$_2$ (25 mL) were consecutively added Et$_3$N (0.89 g, 8.8 mmol) and Me$_3$SiCl 0.96 g, 8.8 mmol). The mixture was stirred at 25° C. for 18 hours and evaporated to dryness under reduced pressure, and the residue was redissolved in dimethyl formamide (30 mL) at the reflux temperature. The solution (solution A) was kept warm throughout the operations described below.

To a suspension of $N^{10}$-formyl-4-amino-4-deoxypteroic acid sesquihydrate (0.732 g, 2 mmol) in dry N-methylpyrrolidinone (35 mL) containing Et$_3$N (0.809 g, 8 mmol) was added tert.-butyloxycarbonyl chloride (273 mg, 2 mmol), and after 15 min of stirring at ambient temperature, one-half of solution A was added. After 10 min, a second portion of tert.-butyloxycarbonyl chloride (137 mg, 1 mmol) was added, followed 20 minutes later by one-quarter of solution A. After another 10 min, a third portion of the same carbonyl chloride (68 mg, 0.5 mmol) was added, followed 15 minutes later by one-eighth of solution A. The last sequence was repeated. After 1 hour MeOH was added and all volatile materials were removed under reduced pressure. The residue was triturated with Et$_2$O (150 mL), and the insoluble material was taken up in a solvent system (5:4:1 CHCl$_3$—MeOH—NH$_4$OH) and applied onto a silica gel column (29×3.0 cm) which was packed and eluted with a second solvent system (14:6:1 CHCl$_3$—MeOH—NH$_4$OH). Fractions containing a major spot at R$_f$ 0.41 (silica gel, 10:6:1 CHCl$_3$—MeOH—NH$_4$OH) along with other lesser spots, were pooled and rechromatographed on a second column (36×3.0 cm) which was eluted with the solvent system 28:12:1 CHCl$_3$—MeOH—NH$_4$OH. Evaporation of pooled fractions containing a single spot at R$_f$ 0.32 (silica gel, 10:6:1 CHCl$_3$—MeOH—NH$_4$OH) yielded starting material (155 mg, 21% recovery). Pooled fractions containing a single spot at R$_f$ 0.41 were evaporated and redissolved in a small volume of MeOH, from which a portion of the product crystallized on standing. The remainder of the product was reprecipitated by adding the mother liquor to Et$_2$O; total yield 494 mg (40%); mp 235° C. (dec); IR (KBr) 3430, 1710 (imide C=O), 1670, 1645 cm$^{-1}$. Anal. (C$_{28}$H$_{25}$N$_9$O$_6$.2H$_2$O) C, H, N. $N^\alpha$-(4-Amino-4-deoxypteroyl)-$N^{67}$-hemi-phthaloyl-L-Ornithine ($N^\delta$-hemiphthaloyl APA—L—Orn)

A solution of the foregoing product (469 mg, 0.757 mmol) in 0.25 N NaOH was maintained at 25° C. for 6.5 hours and the pH was adjusted to 4.3 with 10% acetic acid. The resulting gel was stirred overnight, separated by centrifugation, redissolved in 5:4:1 CHCl$_3$—MeOH—NH$_4$OH, and applied onto a silica gel column (26×2.0 cm) which was then eluted with 10:6:1 CHCl$_3$—MeOH—NH$_4$OH; pooled fractions were evaporated to dryness and the residue was crystallized from EtOH; 122 mg 26% yield). Anal. (C$_{27}$H$_{27}$N$_9$O$_6$.H$_2$O) C, H, N. The product has the structure of Formula I in which R is

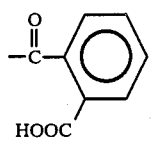

The bioassay sample was obtained from a 40 mg portion of the product purified further by preparative HPLC with 0.1 M ammonium acetate, pH 7.8, containing 8% acetonitrile as the eluent.

Other N$^\delta$-acyl—APA—L Orn compounds not within the scope of the present invention were prepared by condensing N$^{10}$-formyl APA—L—Orn with the various carboxylic anhydrides, followed by alkaline deformylation. They displayed the structure of Formula I above in which R represents the following groups:

| Compound | R |
|---|---|
| 2 | COCH$_3$ |
| 3 | COCH$_2$CH$_2$COOH |
| 4 | COC$_6$H$_5$ |
| 5 | COC$_6$H$_4$Cl-4 |
| 6 | COC$_6$H$_3$Cl$_2$-3,4 |

Inhibition of DHFR purified by MTX affinity chromatography from L 1210/R81 murine leukemia cells was determined. The spectrophotometric assay procedure of Kempton et al., J. Med. Chem., Vol. 25, 475–477 (1982) was used to determine the IC$_{50}$ of methotrexate, aminopterin, and APA—L—Orn as standards or controls and was also used to determine that of compounds 2 to 6 above as well as that of N$^\delta$-hemi-phthaloyl APA—L—Orn, identified as compound 7 in the tables which follow. Certain of the compounds were also tested as inhibitors of partially purified FPGS from mouse liver. The results are summarized in Table 1 below.

TABLE 1

| cmpd | Enzyme Inhibition IC$_{50}$ | |
|---|---|---|
| | DHFR$^a$ | FPGS$^b$ |
| Methotrexate (MTX) | 0.025 | c |
| Aminopterin (AMT) | 0.035 | c |
| 1 APA-L-Orn | 0.072 | 0.15 |
| 2 | 0.028 | 68 |
| 3 | 0.032 | 44 |
| 4 | 0.027 | >100 |
| 5 | 0.028 | — |
| 6 | 0.045 | — |

TABLE 1-continued

| cmpd | Enzyme Inhibition IC$_{50}$ | |
|---|---|---|
| | DHFR$^a$ | FPGS$^b$ |
| 7 | 0.052 | |

$^a$Dihydrofolate Reductase. IC$_{50}$ concentrations (μM) were determined spectrophotometrically at 340 nm as described in Rosowsky et al., Biochem. Pharmacol., Vol. 35, 3327-3333 (1986). Data for 4 and 7 are the means of six separate experiments on different days. The range of values was 0.00056-0.0015 μM for 4 and 0.00011-0.0014 μM for 7.
$^b$Folylpolyglutamate Synthetase. K$_i$ values (μM) were determined as described in Moran et al., Mol. Pharmacol., Vol. 27, pp. 156-166 (1985), using partially purified enzyme from mouse liver in the presence of 500 μM folic acid or AMT as the invariant substrate. The K$_i$ listed for APA-L-Orn is taken from Rosowsky et al., J. Med. Chem., Vol. 29, 655-660 (1986).
$^c$MTX and AMT are substrates for mouse liver FPGS; see Moran et al., supra.

A cytotoxicity assay was carried out for the same group of compounds against L 1210 and L 1210/R81 murine leukemia cells cultured for 48 hours in RPMI 1640 medium containing 10% fetal bovine serum, using the procedure of Mosman, J. Immunol. Meth., Vol. 65, 55–63 (1983). The results are shown in the first two columns of Table 2.

In addition, four of the compounds were tested against human CEM and CEM/MTX lymphoblasts cultured for 48 hours in Dulbecco's modified Eagle's medium containing 10% fetal bovine serum. The IC$_{50}$ (μM) values, with normalized values relative to MTX given in parentheses, are reported in the last two columns of Table 2.

TABLE 2

| CMPD | Cell growth inhibition (IC$_{50}$ in μM)$^a$ | | | |
|---|---|---|---|---|
| | L1210 | L1210/R81 | CEM | CEM/MTX |
| MTX | 0.0046 (1) | 200 (1) | 0.032 (1) | 6.6 (1) |
| AMT | 0.0020 (2.3) | 84 (2.4) | — | — |
| APA-L-Orn | 1.3 (0.0035) | 32 (6.3) | — | — |
| 2 | 0.017 (0.27) | 81 (2.5) | — | — |
| 3 | 0.037 (0.12) | 54 (3.7) | — | — |
| 4 | 0.00089 (5.2) | 17 (12) | 0.0066 (5.0) | 1.1 (6.0) |
| 5 | 0.0032 (1.4) | 27 (7.4) | 0.27 (0.12) | 1.0 (6.6) |
| 6 | 0.032 (0.14) | 127 (1.6) | 7.4 (0.0043) | 10 (0.66) |
| 7 | 0.00075 (6.1) | 52 (3.8) | 0.0043 (7.4) | 0.42 (16) |

$^a$Numbers in parentheses are normalized relative to MTX. Compounds with normalized values less than 1 are more potent than MTX, and vice versa.

The high activity of compound 7 shown in Table 2 was remarkable in view of the fact that the other compounds were all less active even though all displayed virtually the same activity for DHFR, as shown in Table 1.

It is also noteworthy that Compound 7 was 16-fold more potent than MTX against CEM/MTX cells and only 13-fold less potent than MTX against the parental MTX-sensitive cell line.

Methotrexate and γ-tert. -butyl ester of methotrexate as standards or controls, and N$^\delta$-hemi-phthaloyl APA—L—Orn were tested for growth inhibitory activity against MTX-sensitive and MTX-resistant human squamous carcinoma cells by exposing cell monolayers continuously to the drug for about two weeks in accordance with the procedure described in Rosowsky et al., Cancer Res., Vol. 45, 6205–6212 (1985). The IC$_{50}$ (micromolar concentration needed to inhibit cell growth by 50% relative to the controls) results are shown in Table 3, along with the numbers (in parentheses) normalized relative to the IC$_{50}$ of MTX against SCC15 (col. 1 and 2) or SCC25 (col. 3 and 4) cells. The results for the MTX and γ-tert. -butyl ester of MTX compounds are taken from Rosowsky et al., Cancer Res., Vol. 45, 6205–6212 (1985) and J. Med. Chem., Vol. 28, 660–667 (1985), respectively.

TABLE 3

Growth-Inhibitory Activity of Nδ—hemiphthaloyl APA-L-Orn against MTX-sensitive and MTX-resistant Human Squamous Cell Carcinoma Lines in Culture

| cmpd | cells and IC$_{50}$ (μM) | | | |
|---|---|---|---|---|
| | SCC15 | SCC15/R1 | SCC25 | SCC25/R1 |
| MTX | 0.038 (1) | 0.58 (15) | 0.0075 (1) | 0.15 (20) |
| γ-t-butyl ester of MTX | 0.60 (16) | 1.3 (34) | 0.40 (53) | 0.78 (104) |
| 7 | 0.0011 (0.03) | 0.0040 (0.1) | 0.00096 (0.1) | 0.0013 (0.2) |

While the level of resistance to MTX of the two cell lines in Table 3 is lower than that of L 1210/R81 cells or CEM/MTX cells, these test results are relevant because the steep nature of the MTX dose-response in humans means that when a tumor reaches this level of resistance in a patient, further escalation of the MTX dose is not possible. Compound 7 as shown in Table 3 was 10- to 30-fold more potent than MTX against the parental SCC15 and SCC25 cells, while tBMTX was at least 10-fold less potent than MTX. Moreover, while tBMTX was at least 30-fold less potent than MTX against the MTX-resistant SCC15/R1 and SCC25/R1 sublines, the potency of compound 7 against both resistant cells exceeded that of MTX against the parental cells.

What is claimed is:

1. A compound having the structure

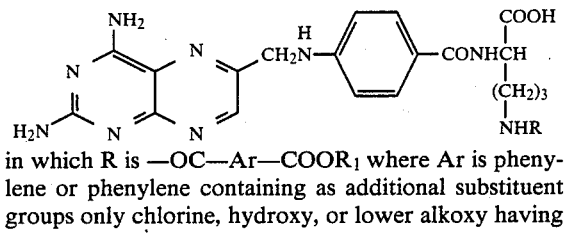

in which R is —OC—Ar—COOR$_1$ where Ar is phenylene or phenylene containing as additional substituent groups only chlorine, hydroxy, or lower alkoxy having 1 to 5 carbon atoms, and R$_1$ is hydrogen or lower alkyl having 1 to 5 carbon atoms.

2. A compound as claimed in claim 1 in which Ar contains as additional substituent groups only chlorine, hydroxy, or lower alkoxy having 1 to 5 carbon atoms.

3. A compound as claimed in claim 1 in which R is

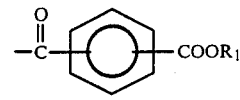

and R$_1$ is hydrogen or lower alkyl having from 1 to 5 carbon atoms.

4. A compound as claimed in claim 1 in which Ar is monocyclic aromatic.

5. A compound as claimed in claim 3 in which R is hemi-phthaloyl.

6. A therapeutic composition exhibiting activity against the growth of methotrexate-resistant cells, said composition consisting essentially of a pharmaceutically acceptable non-toxic carrier and an effective amount of a compound as claimed in claim 1.

7. A therapeutic composition exhibiting activity against the growth of methotrexate-resistant cells, said composition consisting essentially of a pharmaceutically acceptable non-toxic carrier and an effective amount of a compound as claimed in claim 2.

8. A therapeutic composition exhibiting activity against the growth of methotrexate-resistant cells, said composition consisting essentially of a pharmaceutically acceptable non-toxic carrier and an effective amount of a compound as claimed in claim 3.

9. A therapeutic composition exhibiting activity against the growth of methotrexate-resistant cells, said composition consisting essentially of a pharmaceutically acceptable non-toxic carrier and an effective amount of a compound as claimed in claim 4.

10. A therapeutic composition exhibiting activity against the growth of methotrexate-resistant cells, said composition consisting essentially of a pharmaceutically acceptable non-toxic carrier and an effective amount of a compound as claimed in claim 5.

* * * * *

UNITED STATES PATENT AND TRADEMARK OFFICE
CERTIFICATE OF CORRECTION

PATENT NO. : 4,767,761
DATED : August 30, 1988
INVENTOR(S) : Andre Rosowsky

It is certified that error appears in the above-identified patent and that said Letters Patent is hereby corrected as shown below:

Col. 1, line 10, "$N^{\alpha}$-(4amino-4-deoxypteroyl)" should be --$N^{\alpha}$-(4-amino-4-deoxypteroyl)--;

Col. 2, line 10, "dissolved on" should be --dissolved in--;

Col. 2, line 19, "$N^{67}$" should be --$N^{6}$--;

Col. 2, line 64, "$N^{67}$" should be --$N^{6}$--;

Col. 4, line 25, "for" is misspelled;

Claims 2, 4, 7 and 9 were cancelled by amendment and should be deleted.

Signed and Sealed this

Fourteenth Day of February, 1989

*Attest:*

DONALD J. QUIGG

*Attesting Officer*   *Commissioner of Patents and Trademarks*